United States Patent [19]

Folkman et al.

[11] Patent Number: 5,021,404
[45] Date of Patent: Jun. 4, 1991

[54] ANGIOSTATIC COLLAGEN MODULATORS

[75] Inventors: Judah Folkman, Brookline; Donald Ingber, Boston, both of Mass.

[73] Assignee: The Children's Medical Center Corporation, Boston, Mass.

[21] Appl. No.: 183,973

[22] Filed: Apr. 20, 1988

[51] Int. Cl.$^5$ .................. A61K 31/395; A61K 31/44; A61K 31/56; A61K 31/725
[52] U.S. Cl. ..................... 514/26; 514/56; 514/171; 514/210; 514/332; 514/334; 514/365; 514/423; 514/663; 514/725; 514/96
[58] Field of Search .................. 514/26, 56, 171, 210, 514/332, 334, 365, 423, 663, 725, 964

[56] References Cited

U.S. PATENT DOCUMENTS 4,771,042  9/1988  Braughler et al. .................. 514/171

FOREIGN PATENT DOCUMENTS 8704925  8/1987  PCT Int'l Appl. .
8705808  10/1987  PCT Int'l Appl. .

OTHER PUBLICATIONS

Wicha et al; Cancer Letters 12:9–21 (1981).
Crum et al; Science 230:1375–1378 (1985).
Folkman; Advances in Cancer Research 43:175–203 (1985).
Sakamoto et al; Invasion Metastasis 7:208–216 (1987).
Folkman et al; Annal. Surg. 206:374–383 (1987).
Cariou et al; Cell Biology International Reports 12(12):1037–1047 (1988).
Jimenez et al; J. Biol. Chem. 253(5):1420–1426 (1978).
Berg et al; Proc. Natl. Acad. Sci. U.S.A. 77(8):4746–4750 (1980).
Folkman et al; Science 221:719–725 (1983).
Daxenbichler et al; J. Steroid Biochem. 24(1):119–124 (1986).
Ingber et al; Endocrinology 119(4):1768–1775 (1986).
Rizzino et al; In Vitro Cell. & Dev. Biol. 22(12):749–755 (1986).
Ingber et al; In Vitro Cell. & Dev. Biol. 23(5):387–394 (1987).
McAuslan et al; Exp. Cell Res. 176(2):248–257 (Jun. 1988).
Ingber et al; Lab. Invest. 59(1):44–51 (Jul. 1988).
Inoue et al; Carb. Res. 181:135–142 (Oct. 1988).
Doctrow and Kulakowski, Drug News & Perspectives 2:74–81 (1989).
Boutwell et al., Saurat (ed.), New Trends in Research and Therapy, Retinoid Symp., Geneva 1984, pp. 83–96 (Karger, Basel 1985).
Sporn et al. Cancer Res. 43:3034–3040 (1983).

*Primary Examiner*—Ronald W. Griffin
*Assistant Examiner*—Nancy S. Carson

[57] ABSTRACT

Angiostatic compounds are potentiated by collagen matrix metabolism modulators including:
  a) proline analogs which inhibit proline hydroxylation when substituted for proline in collagen;
  b) inhibitors of proline hydroxylase;
  c) inhibitors of collagen cross-linking; and
  d) all trans-retinoic acid.

In methods and therapeutic compositions for inhibiting angiogenesis in a mammal, the collagen matrix modulator is administered with an angiostatic steroid or with heparin (including angiostatic heparin fragments of six or more sugar units, and synthetic fragments).

17 Claims, No Drawings

ANGIOSTATIC COLLAGEN MODULATORS

This invention was supported in part by the United States Government (U.S.P.H.S. Grant CA-37395) and the Government has certain rights in the invention.

BACKGROUND OF THE INVENTION

This invention relates to the general field of controlling angiogenesis—i.e., preventing or treating undesired angiogenesis.

Various diseases are angiogenesis-dependent, in that they are related to the process by which new capillary blood vessels are formed. Uncontrolled and rampant capillary growth can cause extensive tissue damage, e.g. in diabetic retinopathy where neovascularization in the retina may lead to blindness and in rheumatoid arthritis where new vessels in the joint may destroy articular cartilage. Moreover, the progressive growth of tumors generally depends upon continuous induction of angiogenesis.

Folkman, "Tumor Angiogenesis" in *Advances in Cancer Research*, Vol. 43, pp. 175-203 (Klein and Weinhouse, Eds.) generally reviews efforts to find angiogenesis inhibitors which might be used therapeutically, in an effort to control angiogenesis-dependent diseases. Specifically, mixtures of cortisone (or hydrocortisone) and heparin (or heparin fragments) inhibit angiogenesis, as measured by regression of growing capillaries in chick embryo, cessation of tumor-induced capillary growth in rabbit cornea, and regression of some tumors in mice. Folkman et al. *Science* 221:719 (1983). This anti-angiogenic activity is not dependent upon the anticoagulant activity of heparin, nor upon the glucocorticoid or mineralocortocoid activity of steroids. Crum and Folkman, *J. Cell Biol.* 99:158a, Abstr. #581 (1984); and Crum et al. *Science* 230:1375 (1985). The same effect is observed with several natural and synthetic steroids, and they appear to act by inducing basement membrane breakdown, endothelial cell rounding, and capillary retraction. Ingber et al. *Endocrinology* 119:1768 (1986).

Controlled alterations of extracellular matrix metabolism have been suggested as control points in capillary development. Folkman and Ingber, *Annal. Surg.* 206:374 (1987); Ingber et al., *In Vitro Cell Devel. Biol.* 23:387 (1987).

Substitution of certain proline analogs in place of proline in collagen interferes with protein folding, and aberrant triple helix formation results in impaired secretion of interstitial collagens and acceleration of intracellular collagen degradation. Jimenez and Yankrowski, *J. Biol. Chem.* 253:1420 (1978); and Berg et al. *Proc. Nat'l. Acad. Sci. USA* 77:4746 (1980). Incorrectly folded basement membrane collagen may be secreted, but it is not deposited within organized extracellular matrices, Madri and Stenn, *Am. J. Pathol.* 106:180 (1982); Maragoudakis et al. *Biochem. Biophys. Acta.* 538:139 (1978); Wicha et al. *Exp. Cell. Res.* 124:181 (1979); Wicha et al. *Dev. Biol.* 80:253 (1980). Migration of endothelial cells can be inhibited by using proline to interfere with collagen deposition in vitro. Madri et al., cited above. Cells treated with proline analogs exhibit inhibition of collagen deposition into extracellular matrix, although accumulation of non-collagenous protein usually is not significantly affected. Uitto et al. *Arch. Biochem. Biophys.* 173:187 (1976); Blocking basement membrane collagen deposition inhibits growth of 7,12-dimethylbenzanthracene induced rat mammary tumors. Wicha et al. *Cancer Letters* 12:9 (1981).

Proline analogs and $\alpha,\alpha$-dipyridyl (DPY) interfere with morphogenesis of a variety of tissues including cornea (Coulombre and Coulombre, *Dev. Biol.* 28:183 (1972)), cartilage (Aydelotte and Kochmer, *Dev. Biol.* 28:191 (1972)), thyroid gland (Harris et al., *Science* 208:177 (1980)); salivary gland and lung (Spooner and Faubion, *Dev. Biol.* 77:84 (1980)), and mammary gland (Wicha et al., *Dev. Biol.* 80:253 (1980)). Vembu et al., *Exp. Cell Res.* 124:247 (1979); Kidwell et al., "Growth Arrest of Mammary Tumors By Proline Analogs" in *Progress In Cancer Research and Therapy* (Bresciani et al., eds) Vol. 31, p. 129, Raven Press, N.Y., N.Y., 1984.

SUMMARY OF THE INVENTION

We have discovered that certain collagen matrix metabolism modulators potentiate the angiostatic action of other compounds. The invention generally features methods and compositions for inhibiting angiogenesis in a mammal by administering an effective dose of collagen matrix modulator in combination with an angiostatic compound. Collagen matrix modulators useful in the invention include proline analogs which inhibit normal proline hydroxylation when substituted for proline in collagen. Specific proline analogs that are useful include:

a) L-azetidine-2-carboxylic acid (LACA);
b) cis-hydroxyproline (CHP);
c) D,L-3,4-dehydroproline (DHP); and
d) thioproline (TP).

Other useful modulators include inhibitors of prolyl hydroxylase, such as $\alpha,\alpha$-dipyridyl (DPL), and inhibitors of collagen cross-linking, such as $\beta$-aminopropionitrile (BAPN). All trans-retinoic acid, which is known to alter ECM turnover, also potentiates angiostatic compounds.

Angiostatic compounds that are potentiated by the above-described collagen modulators include angiostatic steroids, heparin, heparin oligosaccharide fragments which are hexasaccharides or larger, and heparin analogs having angiostatic properties.

Preferred angiostatic steroids are those described in Crum et al. *Science* 230:1375 (1985) and Ingber et al. *Endocrinology* 119:1768 (1986), including cortisone, epicortisol, hydrocortisone, tetrahydrocortisone S, 17 $\alpha$-hydroxyprogesterone, cortexolone, corticosterone, desoxycorticosterone, hydrocortisol, 6 $\alpha$-fluororo-7,21-dihydroxy-16$\beta$-methylpregna-4,9-(11)-dione-3, 20-dione; 11 $\alpha$-hydrocortisone, 11-desoxycortisol, and 4,9(11) pregnadien-17$\alpha$,21 diol-3,20 dione. Other angiostatic steroids are listed in Table I, accompanying this application.

Heparin, an $\alpha,\beta$ glycosidically linked, highly sulfated copolymer of uronic acid and glucosamine, has been used clinically as an anticoagulant for half a century. The exact structure of heparin has not been elucidated, in part because it is not a homogeneous substance. Heparin is polydisperse with a molecular weight range from 5,000 to 40,000. Within a given chain, there are also structural variations such as varying degrees of sulfation, N-acetylation, and C-5 epimerization in the uronic acid residue.

Consequently, the precise composition of commercial heparin varies depending on its source and method of purification. Heparin has been degraded by treatment with heparinase (an enzyme of bacterial origin, Langer et al., U.S. Pat. No. 4,341,869) which cleaves the molecule at the α-glycosidic linkages between N sulfated-D-glucosamine 6-sulfate and L-iduronic acid 2-sulfate to form fragments including disaccharide, tetrasaccharide, hexasaccharide, and larger oligosaccharides, each being simply a chain-shortened heparin fragment with minor end group modification (the degradation results in a Δ-4,5 site of unsaturation in the terminal uronic acid residue). Linhardt et al., *J. Biol. Chem.*, Vol. 257, 7310-13 (1982).

The invention includes the use in the above-described angiostatic composition of all forms of heparin, and all fragments of heparin having angiostatic effect. See generally Folkman et al., *Science* 221:719-725 (1983). We specifically mean to include heparin fragments which are hexasaccharides or larger. We have also established that synthetic compounds, such as the following, have the desired activity:

loma; childrens hemangioma, angiofibroma and hemophiliac joints; and hypertrophic scars, wound granulation, vascular adhesions, rheumatoid arthritis, scleroderma and atherosclerotic plague.

The preferred compositions are administered orally or parenterally to mammals (e.g. rat, rabbit, monkey man) in forms of e.g. tablets, granules, capsules, injectable solutions, topical creams, and eye-drops.

To treat diabetic retinopathy, for example, the composition can be administered orally or intravenously in the form of a pharmaceutical composition, including a non-toxic pharmacologically acceptable carrier.

Alternatively, the composition can be administered in the form of eye-drops, i.e. one to a few drops per dose can be instilled in the eye with a frequency of 1 to about 4 times a day according to the patient's condition.

For oral administration, the composition can be for-

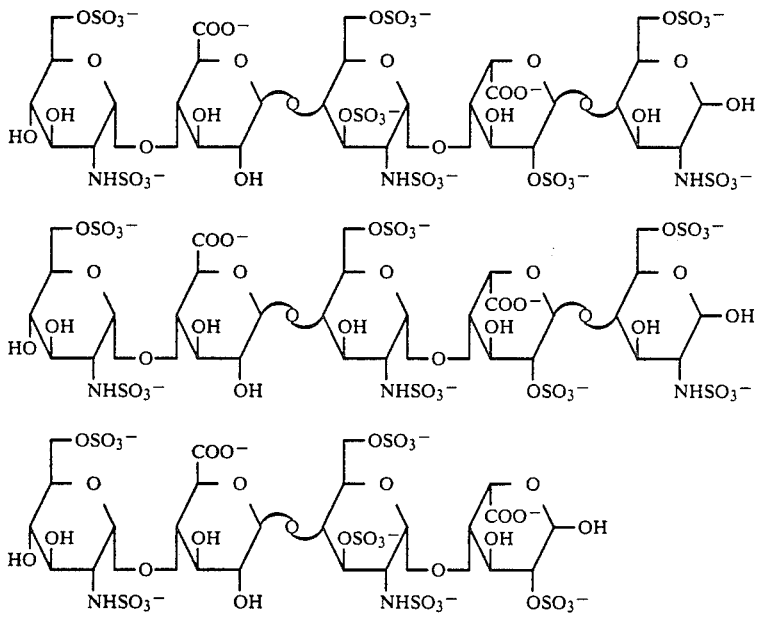

Other features and advantage of the invention will be apparent from the following description of the preferred embodiments.

DESCRIPTION OF THE PREFERRED EMBODIMENTS

In the preferred compositions, the collagen matrix metabolism modulator and the angiostatic compound (preferably either an angiostatic steroid or an angiostatic heparin or heparin-like fragment, or both) are formulated with a physiologically acceptable carrier, depending on the condition being treated and the route of administration. The collagen matrix metabolism modulator is present in a concentration of about 100-250 mg/Kg of body weight/day, depending on its lifetime, and the route of administration.

On the basis of their strong angiostatic activity, the above-described compositions are useful for prophylaxis and treatment of diseases in the fields of ophthalmology, dermatology, pediatrics, surgery and cardiology.

Thus, the compositions may be used for prophylaxis and treatment of neovascularization in diabetic retinopathy, retrolental fibroplasia, corneal graft neovascularization, neovascular glaucoma, ocular tumors, and trachoma; dermatological psoriasis and pyogenic granumulated as a tablet or a capsule together with carrier, diluent or vehicle.

For eye-instillation, the composition can be dissolved in distilled water; the solution may also contain an isotonizing agent, a preservative, or a thickening agent and is adjusted to pH 5 to 9.

The therapeutic composition can also be administered by sustained release techniques, such as sustained release polymers. For example, the composition could be incorporated into an ethylene vinyl acetate copolymer pellet, manufactured by the general technique of Folkman et al. U.S. Pat. No. 4,391,797, which is hereby incorporated by reference. The pellet can be surgically implanted in the tissue to be treated.

EXAMPLES

Modulators of extracellular collagen matrix metabolisms were tested for their ability to induce capillary regression in an assay system using the chick choriollantoic membrane (CAM), which has been previously described. Auerbach et al., *Dev. Biol.* 41:391 (1974); Crum et al., cited above; and Ingber et al. (1986), cited above. The matrix metabolism modulators were administered alone, or in combination with angiostatic steroids and heparin. Generally, methylcellulose sustained drug-release polymers were used for application of test substances on the exposed ectodermal surface of 6 day CAMs. Regression of capillaries within the subectodermal vascular bed resulted in formation of avascular zones (>4mm diameter) within 48 hr of culture (8 day equivalent). Avascular zones were scored using a binocular dissecting scope at 10×magnification (+, 4−6 mm diameter; ++, 6−8 mm; +++, >8 mm).

Cis-hydroxyproline (CHP), L azetidine-2-carboxylic acid (LACA), and D,L-3,4 dehydroproline (DHP) were obtained from Calbiochem (La Jolla, CA). Thioproline (TP) was acquired from Aldrich (Milwaukee, WI). $\alpha,\alpha$-dipyridyl (DPY), $\beta$-aminopropionitrile fumarate (BAPN), and all trans-retinoic acid were purchased from Sigma (St. Louis, MO). Heparin was obtained from (Hepar Inc., Franklin, OH).

Application of the proline analogue, CHP, to the 6 day chick CAM resulted in dose-dependent inhibition of angiogenesis as measured by the percentage of CAMs exhibiting avascular zones on day 8. In general, heparin and angiostatic steroid were applied at 50 μg and 70 μg when used in these studies. CHP induced avascular zones in 100% of CAMs at doses of 600 μg and above. The size (4 to 6 mm diameter) and appearance of these zones were similar to those induced by combinations of angiostatic steroid and heparin (see ref. 23). Other proline analogues (LACA, DHP, and TP) were tested on the CAM and were found to display similar anti angiogenic activity. The proline analogue, DHP, can also alter collagen deposition by inhibiting prolyl hydroxylase activity. Avascular zones were also produced using DPY to interfere with collagen deposition exclusively via inhibition of the enzymes prolyl and lysyl hydroxylase.

When used in suboptimal doses, proline analog greatly potentiated the anti-angiogenic effect of angiostatic steroids and/or heparin. As previously described, combination of angiostatic steroid (e.g. 6α-fluoro-17,21-dihydroxy-16β-methyl-pregna-4,9-(11)-diene-3,20-dione) and heparin produced avascular zones (4–6 mm in diameter) in approximately 40% of CAMs even though each compound has little effect when administered alone.

Coadministration of a half-maximal concentration of LACA (200 μg) with either steroid or heparin resulted in potentiation of anti-angiogenic activity. Addition of LACA (200 μg) to the steroid-heparin combination produced avascular zones in over 90% of CAMs. Zones were also larger in diameter (>6 mm) than those observed with only the steroid-heparin combination and regions outside the zone even exhibited a drastic decrease in capillary density. Combination of heparin and steroid with higher concentrations of either LACA or CHP (>200 μg) induced avascular zones in 100% of CAMs.

The anti angiogenic effects of these drug combinations were found to correlate directly with inhibition of collagen accumulation within 8 day CAMs as estimated by amino acid analysis. In this series of experiments, maximal inhibition of collagen accumulation was observed with combinations of LACA (200 μg), heparin (50 μg), and steroid (70 μg). The same dose of LACA was also able to inhibit collagen deposition when administered alone or in combination with steroid.

L-proline was found to abrogate the effect of the proline analogs, thus confirming that their anti-angiogenic effects resulted from specific perturbation of proline metabolism.

BAPN was tested in the CAM system to directly determine whether alterations of ECM structural integrity could be involved in the anti-angiogenic mechanism. BAPN inhibits collagen cross linking by preventing aldehyde formation and by inhibiting the enzyme lysyl oxidase. An increase in non-cross-linked collagen results in decreased tensile strength of collagenous matrices. BAPN inhibited angiogenesis when administered alone and was as potent as many of the proline analogues. Furthermore, the anti-angiogenic effects of both angiostatic steroids and steroid-heparin combinations were strongly potentiated by low concentrations of BAPN (200 μg) that were inactive when administered alone.

When all trans retinoic acid (Sigma) was tested alone it was found to inhibit angiogenesis in 100% of CAMs at 1 μg. However, it was toxic and resulted in death of embryos at higher doses. Once again, suboptimal doses of retinoic acid potentiated angiostatic steroid and heparin as well as combinations containing proline analogues.

The most effective anti-angiogenic regimens observed in these studies were either (i) angiostatic steroid (70 μg), heparin (50 μg), and LACA (400 μg) or (ii) angiostatic steroid (70 μg), LACA (400 μg), and all trans-retinoic acid (1 μg). The latter combination did not require heparin. Application of methylcellulose polymers containing these anti-angiogenic combinations on 6 d CAM resulted in initiation of zone formation within 24 hr. 100% of CAMs exhibited avascular zones that extended to cover regions over 1 cm in diameter. Avascularity was maintained for an additional 72 hr. This inhibition was reversible since avascular regions always revascularized if maintained in culture for extended periods without readministering drug.

We have shown that inhibition of collagen accumulation is sufficient to induce capillary regression in the growing chick CAM. Specific inhibitors of collagen deposition such as the proline analogues, CHP and LACA, were highly anti-angiogenic when administered alone. In suboptimal doses they were also strong potentiators of angiostatic steroids. Furthermore, anti-angiogenic potency of all drug combinations studied correlated directly with their ability to inhibit collagen accumulation. Capillary involution was similarly produced by DPY, which interferes with collage synthesis by inhibiting prolyl and lysyl hydroxylases.

Proline analogues, on their own, are not preferred chemotherapeutic agents since they can have generalized non-specific effects (e.g., secondary to general protein synthesis inhibition) when administered in high concentrations in vivo. Similarly, retinoic acid is limited by its systemic toxicity at high doses. The importance of the angiostatic steroids in the claimed composition is: 1) they have little if any systemic toxicity, 2) they are potentiated by suboptimal (non-toxic) doses of other matrix modulators, and 3) they apparently can focus the action of general ECM modulators so that their effects are limited only to growing capillaries.

For treatment of diseases (e.g., solid tumors) that depend upon continued neovascularization, angiostatic steroids may be combined with suboptimal doses of the matrix modulators to selectively inhibit the pathological growth of capillaries. Coadministration of angiostatic steroids with these inhibitors of collagen deposition serves to amplify and focus their inhibitory effect on the tumor vasculature. Steroid-matrix modulator combinations that are free of heparin could also be applied topically or in conjunction with sustained drug-release polymer systems, such as those disclosed in Folkman, U.S. Pat. No. 4,164,560, hereby incorporated by reference.

Other embodiments are within the following claims. For example, any one of the collagen matrix metabolism modulators may be combined with any of the angiostatic steroids or any of the heparin fragments or heparin analogs described above.

TABLE I

Angiostatic Steroids

17α,21-dihydroxy-4-pregnene-3,11,20-trione and its 21-acetate (or cortisone)

11α,17,21-trihydroxypregn-4-ene-3,20-dione (or 11α-hydrocortisone)

11β17α,21-trihydroxypregn-4-ene-3,20-dione (or hydrocortisone)

17α,21-dihydroxypregna-4,9(11)-diene-3,20-dione

15α,17α,21-trihydroxy-4-pregnene-3,20-dione

16α,17α,21-trihydroxy-6α-methylpregn4-ene-3,20-dione-21-acetate-16,17 cyclic ketal of acetone 6α-fluoro-17α,21-dihydroxy-16β-methyl-pregna-4,9(11)-diene-3,20-dione 6α-fluoro-17α,21-dihydroxy-16β-methyl-pregna-4,9(11)-diene-3,20-dione-17,21-diacetate 6β,17α,21-trihydroxypregn-4-ene-3,20-dione 17α,21-dihydroxypregn-4-ene-3,20-dione-21-acetate 17α,21-dihydroxypregn-4-ene-3,20-dione 9β,11β-epoxy-17α,21-dihydroxy-2α-methylpregn-4-ene-3,20-dione-21-acetate 17α,21-dihydroxy-16α-methylpregn-4-ene-3, 20-dione 9α,11β-dichloro-17α,21-dihydroxypregn-4-ene-3,20-dione-21-acetate 17α,21-dihydroxy-6α,16α-dimethylpregn-4-ene-3,20-dione-21-acetate 17α,21-dihydroxy-16α-methylpregna-4,9(11)-diene-3,20-dione-21-acetate 17α,21-dihydroxy-16β-methylpregna-4,9(11)-diene-3,20-dione-21-benzoate 17α,21-dihydroxy-6β-methylpregna-4,9(11)-diene-3,20-dione-21-acetate 6α-fluoro-17α,21-dihydroxy-16β-methyl-pregna-4,9(11)-diene-3,20-dione-17-acetate-21-benzoate 17α,21-dihydroxy-16β-methylpregna-1,4, 9(11)-triene-3,20-dione-17-succinate sodium monohydrate 9α-fluoro-11β,16α,17α,21-tetrahydroxy-pregn-4-ene-3,20-dione-16,21-diacetate 17α,21-dihydroxy-16α-methylpregna-1,4,9(11)-triene-3,20-dione-21-succinate sodium monohydrate 6α-fluoro-17α,21-dihydroxy-16β-methyl-pregna-1,4,9(11)-triene-3,20-dione-21succinate sodium

We claim:

1. A method of inhibiting angiogenesis in a mammal by administering to said mammal an angiogenesis-inhibiting dose of a collagen matrix metabolism modulator in combination with an angiostatic compound, said collagen matrix modulator being selected from the group consisting of:

(a) proline analogs which inhibit proline hydroxylation when substituted for proline in collagen;
   (b) inhibitors of proline hydroxylase;
   (c) inhibitors of collagen cross-linking; and
   (d) all trans-retinoic acid;

2. The method of claim 1 wherein said proline analog is selected from the group consisting of: a) L-azetidine-2-carboxylic acid; b) cis-hydroxyproline; c) D,L-3,4-dehydroproline; and d) thioproline.

3. The method of claim 1 wherein said inhibitor of proline hydroxylase is α,α-dipyridyl.

4. The method of claim 1 wherein said inhibitor of collagen cross-linking is β-aminoproprionitrile.

5. The method of any one of claims 1–4 wherein said collagen matrix metabolism modulator is administered in combination with an angiostatic steroid.

6. The method of claim 5 wherein said angiostatic steroid is selected from the group consisting of: cortisone, epicortisol, hydrocortisone, tetrahydrocortisone S, 17α-hydroxyprogesterone, cortexolone, corticosterone, desoxycorticosterone, hydrocortisol, 6α-fluororo-7,21-dihydroxy-16β-methyl pregna4,9-(11)-dione-3,20-dione; 11α-hydrocortisone, 11-desoxycortisol, and 4,9(11) pregnadien-17α,21 diol-3,20 dione.

7. The method of any one of claims 1–4 wherein said angiostatic compound is selected from the group consisting of: heparin; an angiostatic heparin fragment which is a hexasaccharide or larger; or an angiostatic synthetic analog of heparin or of a heparin fragment.

8. The method of claim 1 wherein said collagen matrix metabolism modulator and said angiostatic compound are administered from a sustained release body.

9. A therapeutic composition comprising a mixture of a pharmaceutically acceptable vehicle, a collagen matrix metabolism modulator, and an angiostatic compound, said collagen matrix metabolism modulator being selected from the group consisting of:

a) proline analogs which inhibit proline hydroxylation when substituted for proline in collagen;
   (b) inhibitors of proline hydroxylase; and
   (c) inhibitors of collagen cross-linking 10. The therapeutic composition of claim 9 wherein said proline analog is selected from the group consisting of: a) L-azetidine-2-carboxylic acid; b) cis-hydroxyproline; c) D,L-3,4-dehydroproline; and d) thioproline.

11. The therapeutic composition of claim 9 wherein said inhibitor of proline hydroxylase is α,α-dipyridyl.

12. The therapeutic composition of claim 9 wherein said inhibitor of collagen cross-linking is β-aminoproprionitrile.

13. The therapeutic composition of any one of claims 9–12 wherein said composition comprises an angiostatic steroid.

14. The therapeutic composition of claim 13 wherein said angiostatic steroid is selected from the group consisting of: cortisone, epicortisol, hydrocortisone, tetrahydrocortisone S, 17 α-hydroxyprogesterone, cortexolone, corticosterone, desoxycorticosterone, hydrocortisol, 6 α-fluororo-7,21-dihydroxy-16β-methyl-pregna-4,9-(11)-dione-3,20-dione; 11 α-hydrocortisone, 11-desoxycortisol, and 4,9(11) pregnadien-17α,21 diol-3,20 dione.

15. The therapeutic composition of any one of claims 9–12 wherein said angiostatic compound is selected from the group consisting of: heparin; an angiostatic heparin fragment which is a hexasaccharide or larger; or an angiostatic synthetic analog of heparin or of a heparin fragment.

16. A sustained release body comprising the therapeutic composition of claim 9.

17. The composition of claim 9 further comprising all trans-retinoic acid.

* * * * *